United States Patent [19]

Chen

[11] Patent Number: 5,052,420
[45] Date of Patent: Oct. 1, 1991

[54] TOOTH CLEANER DEVICE FOR RETENTION OF REEL MEANS CARRYING A SPOOL OF STRINGS

[76] Inventor: Raymond Chen, No. 15, Alley 28, Lane 30, Yung Chi Rd., Taipei, Taiwan

[21] Appl. No.: 542,737

[22] Filed: Jun. 22, 1990

[51] Int. Cl.⁵ .............................................. A61C 15/00
[52] U.S. Cl. ................................................... 132/325
[58] Field of Search ............................... 132/325, 323

[56] References Cited

U.S. PATENT DOCUMENTS

| | | | |
|---|---|---|---|
| 1,640,607 | 8/1927 | Kitley | 132/325 |
| 2,047,456 | 7/1936 | Barsch | 132/325 |
| 2,554,526 | 5/1951 | Dembenski | 132/325 |
| 3,734,107 | 5/1973 | Thierman | 132/325 |
| 3,746,017 | 7/1973 | Casselman | 132/325 |
| 3,766,931 | 10/1973 | Fieldes | 132/325 |
| 4,574,823 | 3/1986 | Uriss | 132/325 |

Primary Examiner—Robert P. Swiatek
Assistant Examiner—Nicholas D. Lucchesi
Attorney, Agent, or Firm—Zarley, McKee, Thomte, Voorhees & Sease

[57] ABSTRACT

A tooth cleaner device comprising a frame and cover combination for containing a reel mechanism of the form of a spool of strings or dental floss, a first mechanism for rotatably supporting the reel mechanism and a second mechanism for fixedly positioning and holding a segment of string from the reel mechanism for use. The rotation of the reel mechanism on the frame and cover combination about its axis is controlled by a ratchet mechanism which comprises a pawl in cooperation with a ratchet wheel of the reel mechanism. The string to be used is guided through a channel on the frame from the reel mechanism to a pair of legs constituting the second mechanism and additionally fastened to an anchoring protuberance. A shearing mechanism is disposed on the frame for cutting a used string to be readily disposable.

2 Claims, 3 Drawing Sheets

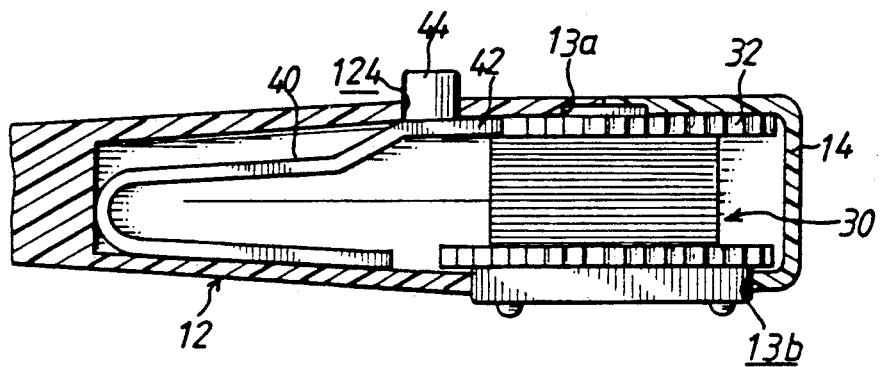
FIG._3A_
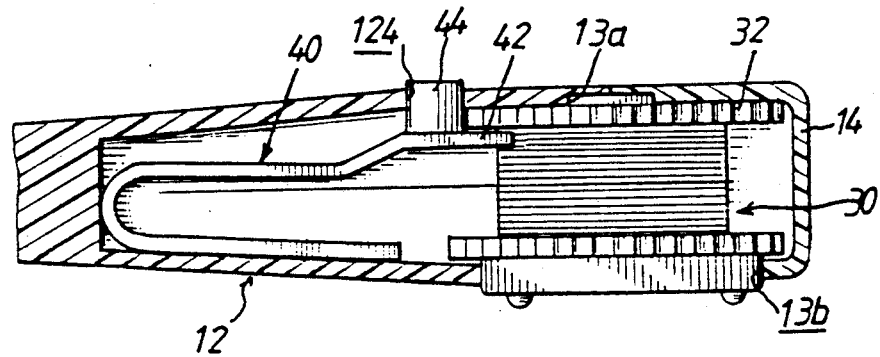
FIG._3B_

TOOTH CLEANER DEVICE FOR RETENTION OF REEL MEANS CARRYING A SPOOL OF STRINGS

BACKGROUND OF THE INVENTION

The present invention relates to tooth cleaner device for storing a spool of strings or dental floss and thereby using the strings for cleaning teeth. More particularly, the present invention relates to tooth cleaner devices which incorporate a first means for rotatably supporting a reel means and a second means for fixedly positioning and holding a segment of strings carried by the reel means.

Devices capable of fixedly positioning and holding a segment of string or dental floss are widely known and utilized. Such devices which utilize a thread-like member of any type for 'flossing' teeth to dislodge and remove adherent material that may develop into plaque are generally designed to be disposable so that the used segment of string or segment floss is not replaceable and the frame of the device can not be used again.

Moreover, a separate spool of strings formed of any suitable type of tooth cleaner has the disadvantage of inconvenience in use since the user must hold both free ends of the string and then pass and pull the string through teeth. Although a loop type tooth cleaner can resolve the above disadvantage, it is still not as convenient as the device which fixedly holds the string in place.

It is the purpose of this present invention, therefore, to provide an improved tooth cleaner device which retains a reel means carrying a spool of any type of string or dental floss thereon. The reel means is rotatably supported on a frame and cover combination of the device. The tooth cleaner device also comprises means for fixedly positioning and holding a segment of string ready for use and the used segment of string can then be sheared or cut by a shearing means provided on the frame. The real means is normally locked in a stationary position by a ratchet means. During use, a pawl of the ratchet means has to be deflected while simultaneously pulling a string carried by the reel means and wrapping it onto a first and second leg having a respective recessed end adapted to stably grip the string. When a segment of string is fixedly positioned on the first and second legs integrally formed on the frame of the present device, the pawl restores to its original position to re-engage the reel means so that the reel means is prevented from rotating.

SUMMARY OF THE INVENTION

Accordingly, it is an object of this invention to provide a tooth cleaner device comprising a first means for rotatably supporting a reel means and a second means for positioning and holding a segment of string from the reel means for use.

A further object of this invention is to provide a tooth cleaner device for the retention of the reel means carrying a spool of strings thereon in which the reel means is rotatable in a controlled manner.

Another object of this invention is to provide a tooth cleaner device for the retention of the reel means carrying a spool of strings thereon in which the segment of string in use is stably gripped by a first and second legs of the frame and the segment of string is readily disposable after use.

These and additional objects, if not set forth specifically herein, will be readily apparent to those skilled in the art from the detailed description provided hereinbelow, with appropriate reference to the accompanying drawings.

BRIEF DESCRIPTION OF THE DRAWINGS

FIG. 3A is a view similar to FIG. 2 but showing a view from the top of the tooth cleaner device of FIG. 1;

FIG. 3B is a view similar to FIG. 3A but showing the ratchet means in a disengaged position;

DETAILED DESCRIPTION OF THE PREFERRED EMBODIMENT.

Figure 1:
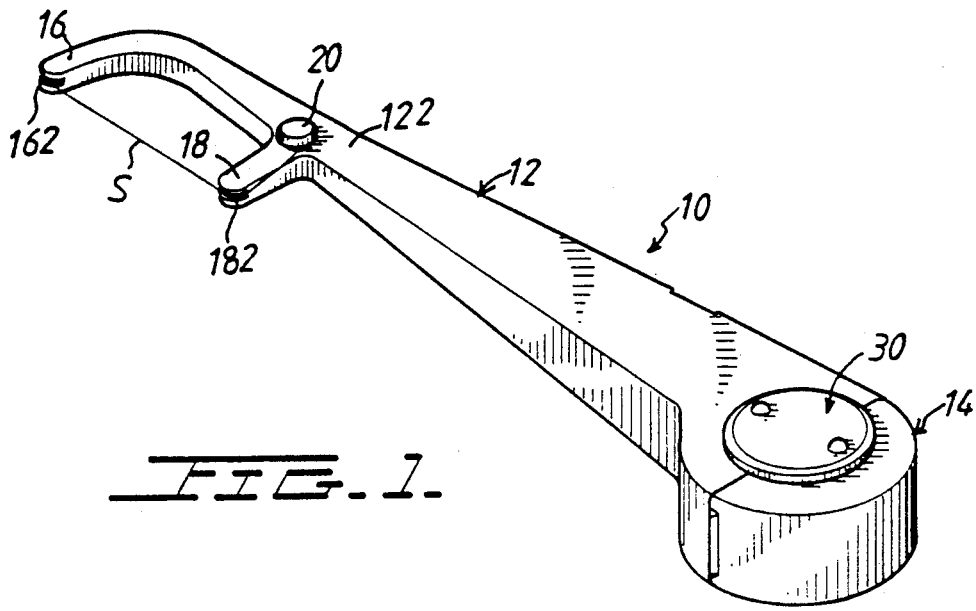
FIG. 1 is a perspective view of a tooth cleaner device used for the retention of a reel means carrying a spool of string or floss in accordance with the invention.
Figure 2:
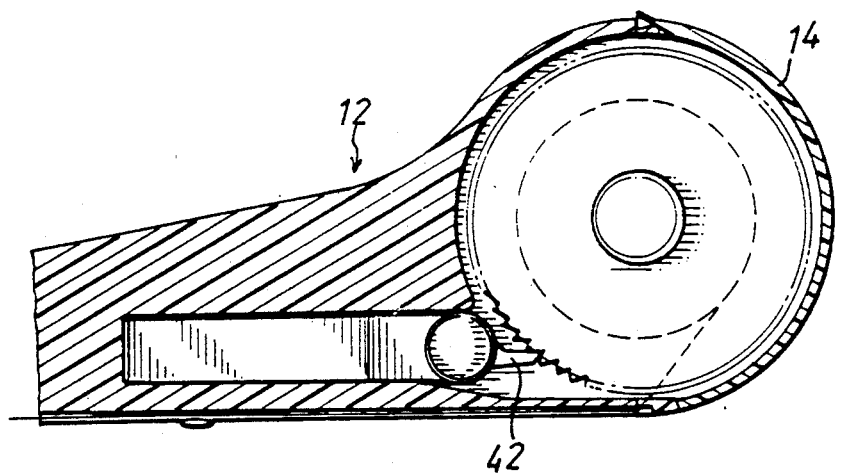
FIG. 2 is a cross-sectional view of the frame and cover combination and the reel means is an enlarged scale, also showing the construction of the ratchet means of the invention, the frame being partly cut away for clarity.

Referring now to the drawings, and more particularly to FIGS. 1 to 3, there is shown the tooth cleaner device, generally designated by reference number 10, which incorporates the preferred embodiment of the present invention. The present device 10 comprises a frame 12 and a cover 14 press-fit together or releasably engageable with each other in a known manner. The frame and cover combination comprises a first and a second leg 16 and 18 having a respective recessed end 162 and 182 for stably positioning and gripping a segment of string (identified by character S) crossed thereover. An anchoring protuberance 20 is provided adjacent to the second leg 18 or the leg which is nearer to a free end of the string segment and offset from the surface 122 of the frame by a suitable gap (also see FIG. 5) to further anchor the free end of the string segment (S). A reel means 30 carrying a spool of strings thereon (cf. FIG. 3) is seen to be accessible from outside.

FIG. 2 shows a section of the frame 12 and cover 14 as well as the reel means 30 in an enlarged scale, in which a portion of the frame 12 is cut away for clarity, while FIG. 3A and 3B are relevant sections. The reel means carrying a spool of strings thereon can be any suitable type and the strings can be any desired design. However, in this embodiment, the reel means 30 used comprises at least a ratchet wheel 32 in cooperation with a pawl 42 of a ratchet means 40 so that the rotation movement of the reel means 30 about its axis and on the frame and cover combination is controlled by the ratchet means 40. As can be seen from FIGS. 3A and 3B, the reel means 30 is rotatably supported on the frame and cover combination by mounting its opposite sides or axles on a cylindrical recess 13a and an opening 13b mutually formed on the frame 12 and the cover 14.

Figure 4:
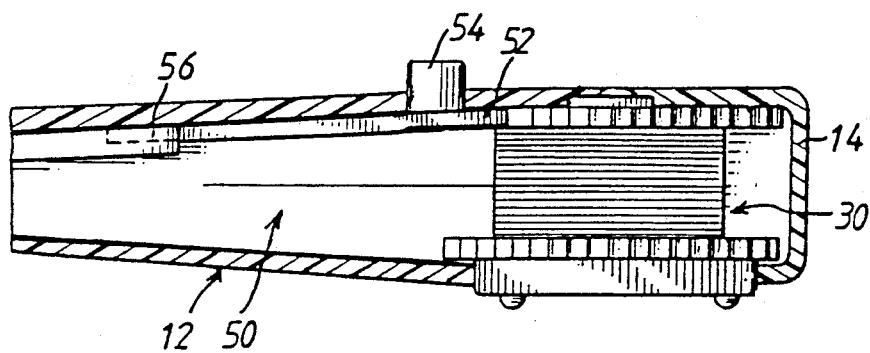
FIG. 4 shows a cross-section of the ratchet means of another embodiment of the invention.

The ratchet means 40 shown in the embodiment of FIG. 3A is substantially U-shaped, with one side formed the pawl 42 and with the other side resting on or in flush with the inner wall of the frame 12. On the pawl 42 there is a lateral dowel or protuberance 44 engaging into a hole 124 provided on the frame 12 and protruding out of the outer surface of the frame 12. It is noted that the ratchet means 40 is flexible so that when in normal or rest position it will be stably received within the frame 12. In this position, the pawl 42 engages with the teeth of the ratchet wheel 32 of the reel means 30 to prevent the reel means 30 from rotation, as shown in FIG. 3A. The pawl 42 is disengaged from the ratchet wheel 32 by the user pressing the protuberance 44 inwards thereby causing the pawl 42 to move an inward distance substantially enough to allow the reel means 30 to rotate freely, as shown in FIG. 3B. FIG. 4 shows another embodiment of the ratchet means 50 comprising a flat plate 56 which has one end fixedly secured on the frame 12 and the opposite end forming a pawl 52 and a lateral dowel or protuberance 54 of similar construction as the previous embodiment.

Figure 5:
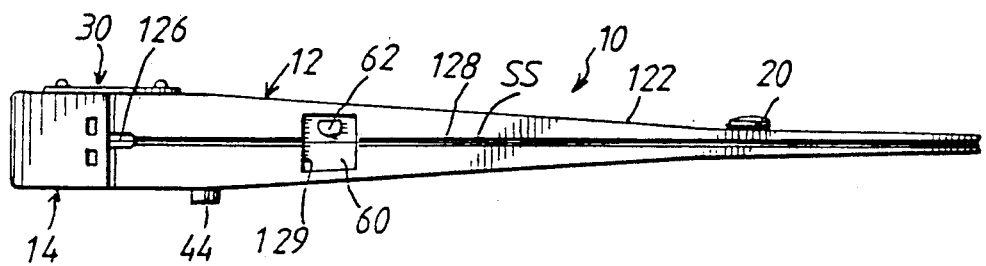
FIG. 5 is a plan view of the tooth cleaner device of FIG. 1, showing the arrangement of the string on the tooth cleaner device of FIG. 1.

FIG. 5 shows a plan view of the device 10 of the invention which further comprises on the frame 12 a string outlet 126 and a channel 128 extending from proximate to the string outlet 126, along a surface of the frame 12, to the recessed end 162 of the first leg 168 which is integrally and continually extending from the frame 12, for guiding the string, identified by character SS, from the reel means 30 to the pair of legs 16 and 18 (cf. FIG. 1). It is understood that the channel 128 is lower than the surface of the frame 12 such that the string (SS) passing in the channel 128 is substantially undisturbed from outside, thereby protecting it from interference. As described above, the free end of the string (SS) can be further wrapped around the anchoring protuberance 20 provided adjacent to the second leg 18 if desired. FIG. 5 also shows a cutter or shearing means 60 which is disposed on a hole 129 of the frame 12. the shearing means 60 is made of metal or any other suitable material and is press-fit to the frame 12. The shearing means 60 comprises a cutter 62, punched and slightly bent outward from the body of the shearing means 60 so that a used segment of string can be readily cut and disposed of.

While the present invention has been explained in relation to its preferred embodiment, it is to be understood that various modification thereof will be apparent to those skilled in the art upon reading this specification. Therefore, it is to be understood that the invention disclosed herein is intended to cover all such modifications as shall fall within the scope of the appended claims.

I claim:

1. In a tooth cleaner device having a reel means carrying a spool of strings thereon and provided with a ratchet wheel, a frame and cover combination rotatably supporting said reel means and being capable of fixedly supporting and holding a segment of string from said reel means, and a ratchet means for controlling a rotation of said reel means relative to said frame and cover combination, the improvement comprising:

said frame and cover combination comprising a cylindrical recess and an opening for mounting said reel means and said opening exposing a side of the reel means to allow manual manipulation of said reel means, a pair of legs each having a recessed end, a string outlet, a channel thereon extending from said string outlet to said recessed ends of said legs, and an anchoring protuberance provided adjacent to said legs for anchoring the free end of the string segment; and said ratchet means comprising a pawl releasably engaged with said ratchet wheel of the reel means, said pawl having a lateral protuberance engaged in a hole of said frame and cover combination so that said pawl is laterally manipulatable in a direction generally parallel to a rotational axis of the reel means to control the free rotation of said reel means, said ratchet means being substantially a flat plate with one end thereof forming said pawl and a second end thereof being fixedly secured on said frame and cover combination.

2. In a tooth cleaner device having a reel means carrying a spool of strings thereon and provided with a ratchet wheel, a frame and cover combination rotatably supporting said reel means and being capable of fixedly supporting and holding a segment of string from said reel means, and a ratchet means for controlling a rotation of said reel means relative to said frame and cover combination, the improvement comprising: said frame and cover combination comprising a cylindrical recess and an opening for mounting said reel means and said opening exposing a side of the reel means to allow manual manipulation of said reel means, a pair of legs each having a recessed end, a string outlet, a channel thereon extending from said string outlet to said recessed ends of said legs, and an anchoring protuberance provided adjacent to said legs for anchoring the free end of the string segment; and said ratchet means comprising a pawl releasably engaged with said ratchet wheel of the reel means, said pawl having a lateral protuberance engaged in a hole of said frame and cover combination so that said pawl is laterally manipulatable to control the free rotation of said reel means, said ratchet means being substantially a U-shaped plate with one side thereof forming said pawl and a second side thereof fixedly secured on said frame and cover combination.

* * * * *